(12) United States Patent
Peria (10) Patent No.: US 8,402,828 B2
(45) Date of Patent: Mar. 26, 2013

(54) MICROSCOPIC ACOUSTIC RADIATION DETECTING APPARATUS AND METHOD

(76) Inventor: William J. Peria, Seattle, WA (US)

( * ) Notice: Subject to any disclaimer, the term of this patent is extended or adjusted under 35 U.S.C. 154(b) by 444 days.

(21) Appl. No.: 12/776,640

(22) Filed: May 10, 2010

(65) Prior Publication Data

US 2010/0218610 A1 Sep. 2, 2010

Related U.S. Application Data

(63) Continuation-in-part of application No. 11/844,285, filed on Aug. 23, 2007, now abandoned.

(60) Provisional application No. 60/824,259, filed on Aug. 31, 2006.

(51) Int. Cl.
*G01N 29/14* (2006.01)

(52) U.S. Cl. ............................................. 73/590; 73/643

(58) Field of Classification Search ............... 73/590, 73/587, 588, 643, 655, 657
See application file for complete search history.

(56) References Cited

U.S. PATENT DOCUMENTS

| | | | | |
|---|---|---|---|---|
| 3,782,176 A | * | 1/1974 | Jacobs | 73/657 |
| 4,208,914 A | * | 6/1980 | Feist | 73/590 |
| 5,656,428 A | * | 8/1997 | McAllister et al. | 435/6.11 |
| 6,215,551 B1 | * | 4/2001 | Nikoonahad et al. | 356/237.2 |
| 2003/0049693 A1 | * | 3/2003 | Goh et al. | 435/7.9 |
| 2008/0252884 A1 | * | 10/2008 | Carr | 356/318 |

OTHER PUBLICATIONS

Haisch C et al, "Light and sound—photoacoustic spectroscopy," Spectroscopy Europe vol. 14 No. 5 (2002), pp. 10-15.

* cited by examiner

*Primary Examiner* — Peter Macchiarolo
*Assistant Examiner* — Rose M Miller
(74) *Attorney, Agent, or Firm* — Aeon Law; Adam L. K. Philipp (57) ABSTRACT

A macromolecular docking event between a macromolecule of a first type (e.g. an antibody) and a macromolecule of a complementary type (e.g., an antigen) may be detected by dispersing macromolecules of the first type in a microscopic test region within an aqueous test volume and introducing at least one macromolecule of the complementary type into the microscopic test region. When the complementary macromolecule docks with one of the macromolecules of the first type, micro-acoustic radiation propagating through the microscopic test region is detected and the micro-acoustic wave emitted by the macromolecular docking is identified. Methods and apparatuses for detecting macromolecular docking events in such a manner are described.

17 Claims, 9 Drawing Sheets

MICROSCOPIC ACOUSTIC RADIATION DETECTING APPARATUS AND METHOD

CROSS REFERENCE TO RELATED APPLICATIONS

This application is a continuation-in-part of prior application Ser. No. 11/844,285 (pending), filed Aug. 23, 2007, titled "Microscopic Acoustic Radiation Detecting Apparatus and Method," and naming inventor William J. Peria. Prior application Ser. No. 11/844,285 claims the benefit of priority to Provisional Application No. 60/824,259 filed Aug. 31, 2006, titled "Microscopic Acoustic Radiation Detecting Apparatus and Method," and naming inventor William J. Peria. The above-cited applications are incorporated herein by reference in their entirety, for all purposes.

FIELD

This application relates to methods and apparatuses for studying small macromolecular samples, and more particularly, to methods and apparatuses for detecting micro-acoustic radiation emitted by individual macromolecular transition events.

BACKGROUND

The final result of many experiments in modern biology is a measurement of the expression profile of cultures of cells which have been treated in specifically prescribed ways. In other words, how did the cells in the culture respond to a given set of conditions? What enzymes or other proteins did they produce, and in what quantities? Did they fail to produce particular proteins? If one could grow cells individually rather than in cultures, exposing each to slightly different conditions throughout its life cycle, and then accurately measure the expression profile of each single cell separately, progress on the many open questions in modern biology would accelerate significantly. The quantitation of proteins is currently done with Tandem Mass Spectrometry (MS/MS). MS/MS requires large sample sizes, usually larger than what is available from a single cell. However, the data from MS/MS are often ambiguous, and the protein content of a sample may be reconstructed from the mass spectrum using various techniques, such as time-consuming maximum likelihood methods.

Many technologies exist for the detection of various biological processes and events. Circular dichroism spectroscopy (CD) can detect large changes in the folded fraction of a bulk sample of proteins in solution, for proteins which fold at modest speeds. But a CD spectrum represents only an average over many molecules, and does not yield any information on the folding process in a single molecule. To track fast-folding proteins, CD requires an intense and costly light source (such as the ALS at the Lawrence Berkeley Lab), but again, only the aggregate folded fraction is detected, not single protein molecules.

Fluorescence Resonant Energy Transfer (FRET) is a single molecule method which can track the progress of a folding protein, but it yields information about a limited number of residues only, a small fraction of the number found in a typical globular protein. Furthermore, the information from FRET is simply that pairs of residues either are or are not in close contact, and to some extent, how close that contact is. Hence, FRET measures only degree of progress along the path to the native state, and does not supply information about the nature of the processes which lead to the native state.

"Yeast Songs" can be detected with Atomic Force Microscopy (AFM), but only up to frequencies significantly less than 100 kHz. Furthermore, AFM requires direct mechanical contact with a yeast cell in vivo.

The sequencing of nucleic acids currently requires a substantial amount of sample material, which may usually be amplified via the polymerase chain reaction (PCR). At present, several minutes are needed to determine a single nucleotide in a sequence with reasonable confidence. Thus, the determination of sequences of significant lengths requires a high degree of parallelization and automation.

In some fields, the technique of photoacoustic spectroscopy may be used to study certain bulk properties of quantities of some type of molecule within a medium. In photoacoustic spectroscopy, an intense laser is cyclically pulsed through a transparent medium, which contains a quantity of some type of molecule under study. Energy from the intense laser pulses is transferred to some of the molecules under study, causing them to rapidly heat and cool. This rapid heating/cooling cycle results in cyclical thermal expansion/contraction of the sample. The resulting pressure waves are typically amplified by an acoustic resonance of the test chamber before being detected by sensitive transducers. However, photoacoustic spectroscopy is not suitable for studying non-cyclical events involving one or only a small number of molecules, especially those involving a macromolecule of life transitioning from one inherent, stable state to another inherent, stable state (e.g., a protein folding, an antibody binding to an antigen, DNA supercoiling, DNA replication, and the like).

DESCRIPTION

Various embodiments described herein provide an instrument capable of detecting acoustic radiation from microscopic sources ("micro-acoustic radiation"), which would enable advances in several areas. For example, in some embodiments, one could determine the protein (enzymes and the like) composition of very small volume samples, enabling single-cell biological experimentation. The step-by-step detailed temporal history of numerous cellular processes could be studied. The folding of single protein molecules could be tracked in real time. Metabolically-driven motions of the cell walls of yeast ("yeast songs") could be detected and monitored with bandwidths of 1 MHZ or more, in vivo and without mechanical contact. Clues as to the functioning of flagella and other motor proteins could be obtained. The docking of enzymes could be detected, and protein-protein interactions could be detected, specified, and their processes revealed. A catalog of characteristic "sound signatures" typical of some or all of these processes could be produced. In particular, the cataloguing of the sounds produced by the folding of known proteins would allow for protein quantitation in cellular or even sub-cellular volume samples of unknown composition. Nucleic acids could be sequenced at the same rate at which they are synthesized by their polymerases. A single nucleic acid strand would represent a sufficient quantity of material for sequencing, whether for forensic or clinical purposes.

Figure 1A:
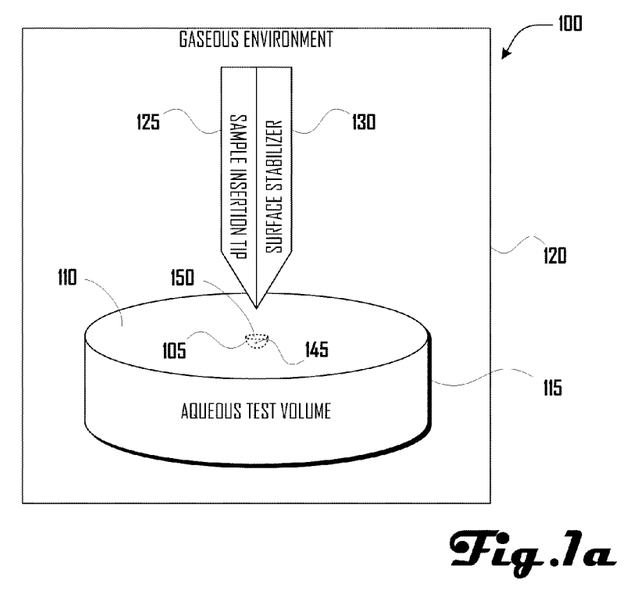
FIGS. 1a and 1b illustrate an exemplary system for detecting micro-acoustic radiation emitted by a macromolecular sample in accordance with one embodiment.

FIG. 1a illustrates an exemplary system 100 for detecting micro-acoustic radiation emitted by a macromolecular sample 145 in accordance with one embodiment. The illustrated system 100 includes an aqueous test volume 115 within a gaseous environment 120. The amount of aqueous liquid in the aqueous test volume 115 is not critical, but in one embodiment, a relatively large volume (approximately 0.2 liter) of aqueous liquid is used to fill aqueous test volume 115 so that solid surfaces (e.g., the bottom and sides of the vessel containing aqueous test volume 115), where non-specific binding might occur, are comparatively far away from the test region 105. In other embodiments, a larger or smaller aqueous test volume 115 may be employed.

In various embodiments, aqueous test volume 115 may comprise pure water, a saline solution, or another water-containing liquid suitable for hosting the macromolecule under study and providing an environment in which the desired macromolecular event may take place.

A surface stabilizer 130 is positioned and configured to stabilize the elevation of the target area 150 within the surface 110 of aqueous test volume 115. In some embodiments, stabilizing the elevation of the target area 150 comprises controlling low frequency "bathtub modes" (waves of a few microns amplitude at frequencies of roughly 10 Hz), at least in the region of sensitivity near target area 150. In one embodiment, surface stabilizer 130 holds the target area 150 to an elevation within a range of about +/−15 nanometers. In other embodiments, surface stabilizer 130 holds the target area 150 to an elevation within a range of about +/−7.5 nanometers or to an even smaller range.

In some embodiments, surface stabilizer 130 may also include other isolation devices, such as a mechanical isolation system (not shown). In some embodiments, a mechanical isolation system may be desirable to prevent or minimize external sources of acceleration from perturbing the sample. In some embodiments, a standard pneumatic table is suitable (e.g., a MICRO-G #14088 from Kurashiki Corp. of Japan). In some embodiments, an enclosure (not shown) may be constructed (e.g. from glass, Lucite, and/or other suitable material) around the entire apparatus to isolate the surface 110 of aqueous test volume 115 from stray air currents, and the like.

A sample insertion tip 125 is positioned and configured to introduce a macromolecular sample 145 comprising one or more macromolecules into a test region 105 within aqueous test volume 115.

In various embodiments, sample insertion tip 125 may comprise a generic sample holder adaptable for general purposes. In alternate embodiments, a microfluidic system for introducing fluid samples of various kinds may be employed. In one embodiment, electrospray ionization ("ESI"), a mature technology used for mass spectrometry of proteins, may be deployed to control the introduction of small amounts of a macromolecular sample into test region 105. In one embodiment, droplets delivered via an ESI tip or needle to the target area surface 150 have only enough momentum to penetrate to a depth of less than one micron; thus, the macromolecules may be delivered to the test region 105, where they can be observed, as disclosed herein.

In one embodiment, sample insertion tip 125 may be positioned within 0.1 millimeter above the target area surface 150. In other embodiments, sample insertion tip 125 may be positioned within 0.5 millimeter above the target area surface 150. In still other embodiments, sample insertion tip 125 may be positioned closer or further from the target area surface 150, partially or fully above target area surface 150 (i.e., partially or fully within gaseous environment 120) and/or partially or fully below target area surface 150 (i.e. partially or fully within aqueous test volume 115).

In some embodiments, surface stabilizer 130 and sample insertion tip 125 may be combined. For example, in one embodiment, surface stabilizer 130 and sample insertion tip 125 may comprise a single electrospray ionization tip.

In many embodiments, the macromolecular sample 145 may include one or more large molecules of life, e.g., proteins, nucleic acids, and the like. In various embodiments, such macromolecules may emit "audible" or detectable or identifiable micro-acoustic waves during macromolecular events that involve an abrupt settling of the macromolecule into a lower energy state. In many macromolecular systems (including many in living cells), such transitions from one macromolecular state to another may involve abrupt motions of rigid molecular components—components that are typically orders of magnitude larger than a water molecule. Exemplary abrupt motions include the folding of proteins, the docking of enzymes, the spinning of flagella, the supercoiling of DNA, the addition of nucleotides during nucleic acid synthesis, and the like. Each of these motions involves the simultaneous acceleration of hundreds or thousands of neighboring water molecules, with energies comparable to or larger than the thermal energy in the surrounding test region 105. In other words, many macromolecular transitions create a synchronous localized perturbation of the momenta of many molecules in a fluid medium. Such a perturbation (the direct transfer of momentum from a macromolecule to its surrounding molecules) then propagates away from the source as a micro-acoustic wave 155.

Put another way, such macromolecular transition events may also be intimately linked with the processes vital to life. For example, the energy that binds an antibody to its antigen, that holds a protein folded in its native state, or that attaches nucleotides to a template DNA strand must be released into the surrounding environment in the course of the corresponding transition event. Ultimately the energy thus released becomes entropy or heat, but in the immediate vicinity (i.e., within test region 105) of the macromolecular transition event, there will be a tiny but highly ordered "nudge" emitted by the transitioning macromolecule 145 (see also macromolecules 545, 645, and 745 in FIGS. 5-7, respectively) to nearby molecules (not shown—mostly water molecules in many embodiments). This nudge is then passed along to the nearby molecules' neighbors as a tiny, but detectable micro-acoustic wave 155 (see also waves 555, 655, and 755 in FIGS. 5-7, respectively). Micro-acoustic wave 155 propagates through test region 105 until it meets target area surface 150, causing the elevation of target area surface 150 to ripple or oscillate slightly, which ripples or elevation oscillations are detectable by detector 135. In some embodiments, elevation changes of target area surface 150 between 0.1 nanometer and 10 nanometer may be reliably detected.

In one embodiment, target area 150 may be roughly circular, with a radius of approximately 10 micrometers (or 10 microns). Similarly, in one embodiment, test region 105 may correspond roughly to a hemisphere with a radius of approximately 10 micrometers. Test region 105 does not have a fixed or physical boundary; rather, test region 105 is merely the portion of aqueous test volume 115 that is so close to target area 150 that the micro-acoustic wave 155 remains detectable by detector 135 and identifiable by identifier 140. In other words, while macromolecular transition events may happen elsewhere within aqueous test volume 115, the micro-acoustic waves emitted by these distant events may have decayed to the point that it is no longer detectable and/or identifiable by the time the wave propagates through test region 105.

In exemplary embodiments, the macromolecular sample 145 is introduced into test region 105 by sample insertion tip 135, and while the macromolecular sample 145 is within the test region, the macromolecular sample 145 is provoked to abruptly transition from one state to another state (e.g., a protein molecule is provoked to fold, a DNA molecule is provoked to interact with a polymerase complex, an antibody is provoked to dock with an antigen, and the like), emitting a micro-acoustic wave, as discussed above.

Figure 1B:
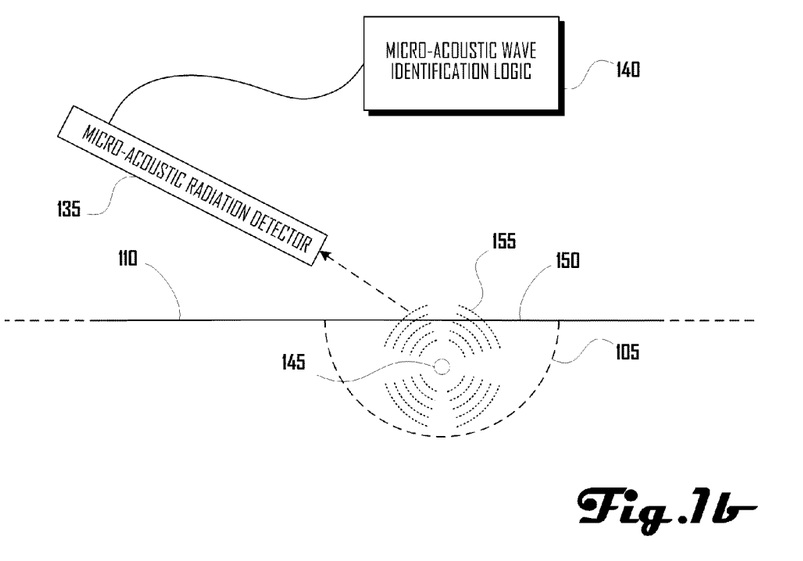
Figure 4A:
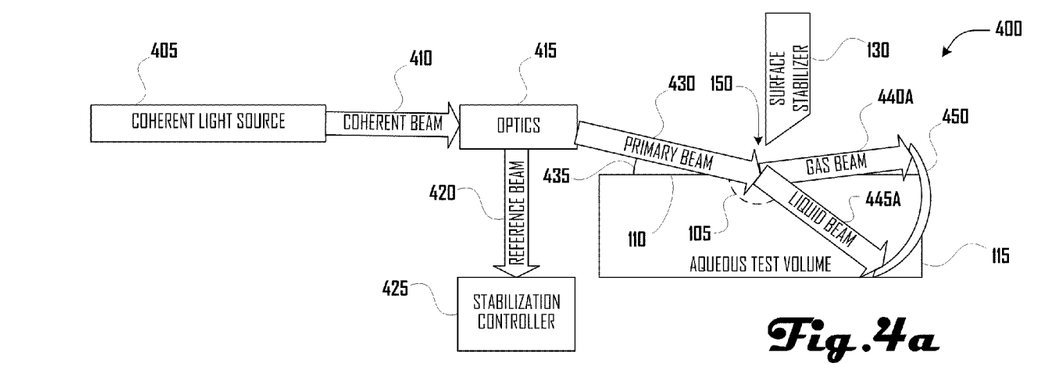
FIGS. 4a and 4b illustrate a laser-interferometer-based micro-acoustic radiation detector in accordance with one embodiment.

As illustrated in FIG. 1b, detector 135 is focused on and detects micro-acoustic radiation propagating through the test region 105 of aqueous test volume 115, which micro-acoustic radiation manifests essentially as ripples on the target area 150 of surface 110. (FIG. 4, discussed below, illustrates an exemplary laser-interferometer-based embodiment of micro-acoustic radiation detector 135.) Micro-acoustic wave identification logic 140 identifies, in the detected micro-acoustic radiation, the micro-acoustic wave 155 emitted by macromolecular sample 145 when it transitions from one state to another within test region 105 of aqueous test volume 115.

In general, to be detectable, a micro-acoustic wave 155 must have pressure perturbations that exceed those due to thermal agitation within test region 105. The power spectrum for thermal pressure fluctuations in unbounded pure water is given by Equation 1.

$$p(\omega)^2 = \frac{kT\rho}{4\pi^2} \frac{\omega^2}{c} \frac{1}{1+u^2} \quad \text{Equation 1}$$

In Equation 1, kT is the thermal energy, $\rho$ is the density of water, c is the speed of sound in water, $\omega$ is the frequency (times $2\pi$), and u is the dimensionless ratio $\omega r_t/c$ which relates the transducer size $r_t$ to the wavelength of the noise component in question. This represents a fundamental limit on the detectability of acoustic signals from macromolecules.

The principles of acoustics at low Reynolds number (meaning that the fluid's viscosity controls its dynamics) give the equation for the instantaneous pressure perturbation generated by a sphere moving along an axis with arbitrary time dependence as in Equation 2.

$$p(r, \theta, t) = \frac{3}{2} a\mu \frac{\cos\theta}{r^2} \left( \frac{r}{c} \frac{\partial \vec{v}_c(t-r/c)}{\partial t} + \vec{v}_c(t-r/c) \right) \quad \text{Equation 2}$$

In Equation 2, $\mu$ is the dynamic viscosity of water, a is the radius of the moving sphere, r is the distance from the sphere's center to the observation point in a direction inclined at an angle $\theta$ to the axis of the sphere's motion, and $\vec{v}_c$ is the velocity of the sphere's center, to be evaluated at the retarded time (t−r/c). In essence, Equation 2 says that the sphere's motion at time t is directly coupled to a pressure perturbation observed later (at t−r/c) at a point that is displaced from the sphere's center by a distance r in a direction given by $\theta$. Equation 2 is essentially a statement of the conservation of momentum, so it is expected to be valid at macromolecular scales.

To make a useful comparison to the thermal molecular noise presented above in Equation 1, a sinusoidal dependence with an arbitrary frequency and amplitude was used to build a power spectrum from Equation 2. Two choices were made for the amplitude, each of which applies to a different frequency range. First, an object of a certain size, e.g. a piece of a folding protein (here approximated as a sphere of radius a, with a of the order of a few nanometers), as it diffuses about the energy landscape during folding, will move with an amplitude on the order of its own size. I.e., a is also a reasonable choice for the amplitude. (This may overestimate the amplitude of some motions, like side chain rotations, but it almost certainly underestimates the amplitudes of others, like backbone motions or hydrophobic collapse.) This constant amplitude assumption may not be realistic at high frequencies, where the corresponding required energy rises very rapidly. A second choice of amplitude solves this: a constant energy assumption, in which the energy dissipated per cycle against viscous drag is held fixed at a constant multiple of the thermal energy kT, independent of frequency. This constant energy assumption becomes nonsensical at low frequencies, where it translates to very large amplitudes of motion. So, a fixed amplitude of a is chosen for low frequencies, crossing over to a fixed energy of $\epsilon kT$ at high frequencies, where $\epsilon$ is a number between one and roughly 60, depending on the particular process being considered.

Equation 1 and Equation 2 may be combined to give the signal-to-noise ratio ("SNR") as in Equation 3. Although this expression for the SNR was derived in terms of pressure amplitudes, it will also be appropriate for phenomena which are driven directly by pressure perturbations (e.g. fluid velocity perturbations).

$$SNR(\omega) = 6\mu \frac{ad}{r^2}(1+u^2)\sqrt{\frac{\pi c}{\rho kT\omega}} \quad \text{Equation 3}$$

For the constant amplitude model appropriate for low frequencies, the motion amplitude d may be replaced with the source size a in the Equation 3, while the constant energy model yields a more complex function of frequency for d. The dynamic viscosity $\mu$ may affect the generation of a measurable signal. At low Reynolds number, viscosity serves to significantly increase the effective source size by increasing the size of the region over which correlated velocity perturbations are induced by a given source motion. Without viscosity, relatively slow source motions such as those considered here may not generate detectable sound. Furthermore, it may be the case that in regions within one nanometer of a moving macromolecule, the dynamic viscosity of water is elevated relative to its value in the bulk. If so, this might tend to actually increase the amplitude of the observed signals, but such potential enhancement effects were not included here.

In various embodiments, the micro-acoustic wave 155 emitted by macromolecule 145 inside test region 105 may be detected and/or identified with varying degrees of fidelity. In one embodiment, merely a "click" (as in a Geiger counter) may be detected and/or identified. In one embodiment, such a "click" may signal that a macromolecular docking or binding event has occurred. For example, a detected "click" may signal that one or more proteins, enzymes and/or antibodies/antigens has docked to a complementary macromolecule. (See FIG. 5, discussed below.) In another embodiment, such a "click" may signal that a macromolecule has changed shape. (See FIG. 6, discussed below.) Such detection of simple "click" micro-acoustic waves may facilitate the detection of, e.g., a particular target antibody or antigen associated with a particular disease condition or treatment as it binds to its specific partner.

Accordingly, various embodiments may streamline biomarker tests, such as are commonly used for detection and/or treatment monitoring of certain infectious diseases, cancers, or other conditions. One embodiment may be used to detect the presence of such markers in clinical samples by introducing both the sample and the complement into the instrument and detecting the subsequent docking events (if any) by detecting micro-acoustic radiation emitted as a consequence of the docking event. (See FIG. 5, discussed below.) Essentially any current or future clinical test that involves specific binding to a large target molecule could be carried out using various embodiments to acoustically detect binding events in solution, without tagging by fluorescence or other means.

In other embodiments, the detected micro-acoustic radiation may signal more than the mere occurrence of a macromolecular docking or binding event. For example, using the detected micro-acoustic radiation, it may be possible to distinguish different types of binding events. Accordingly, in some embodiments, it may be possible to perform an assay for several targets at once. In other embodiments, it may be possible to distinguish one class of protein from another in a sample. In other words, proteins from clinical or research lab samples could be introduced into the test region 105 and induced to fold. The sounds of the formation of the different secondary structures (e.g. helices and sheets) may be distinguishable. In some embodiments, it may even be possible to measure the complete gene expression profile from a single cell in this manner.

In still other embodiments, it may be possible to detect four distinct sounds associated respectively with the attachment of the four nucleotide bases (the "letters") to a DNA template strand. In such embodiments, it may be possible to sequence DNA at the replication rate, without amplification or tagging, by "listening" to the micro-acoustic radiation emitted during the interaction between the DNA and its polymerase complex. (See FIG. 7, discussed below.)

Thus, in many embodiments, a micro-acoustic wave 155 emitted by a macromolecular event may be a complex signal, comprising one or many components in the time and/or frequency domain.

Figure 2:
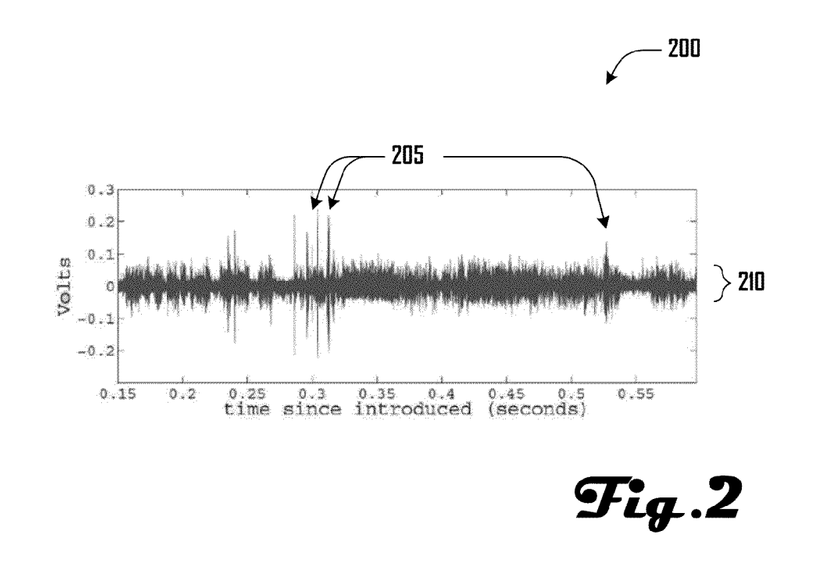
FIG. 2 illustrates a waveform of micro-acoustic radiation identified by a prototype micro-acoustic radiation detection system in accordance with one embodiment.

For example, FIG. 2 illustrates a waveform 200 of micro-acoustic radiation detected by a prototype embodiment of detector 400 (see FIG. 4, discussed below). Within the detected micro-acoustic radiation, a signal 205 has been identified above the thermal molecular noise floor 210. The identified signal 205 likely corresponds to a micro-acoustic wave emitted by a molecule of DNA during supercoiling. Signal 205 is consistent with lengthwise dragging of the major groove past the target area surface 150 at tens of microns per second.

Figure 3:
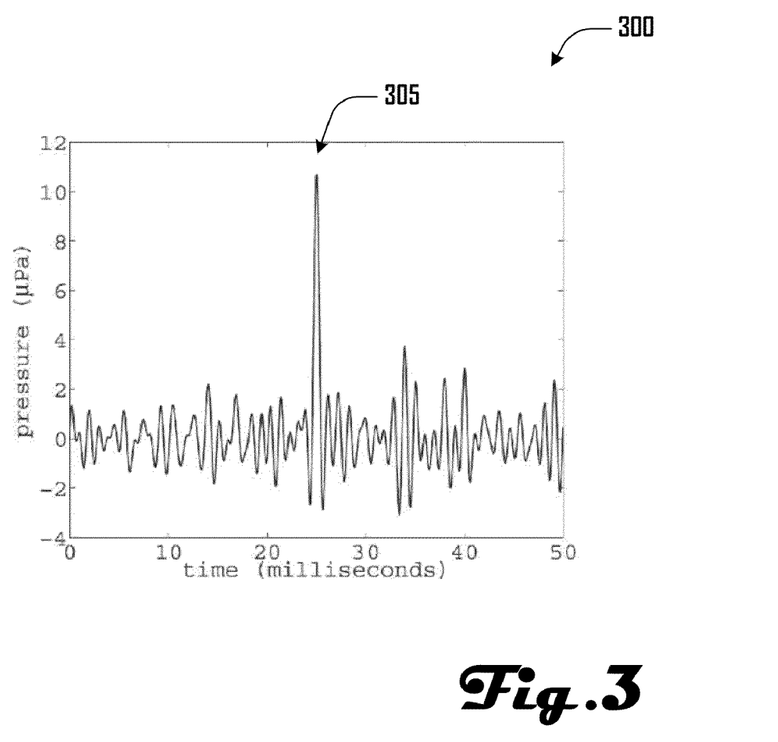
FIG. 3 illustrates a time series of micro-acoustic radiation obtained from computationally simulating a docking event between two proteins in accordance with a simulated embodiment of a micro-acoustic radiation detection system.

FIG. 3 illustrates a time series of micro-acoustic radiation obtained from computationally simulating a docking event between two proteins, in accordance with a simulated embodiment of system 100 and the principles set out in Equations 1-3 (above). In some embodiments, docking between two (or more) proteins produces a micro-acoustic wave that is proportional to the difference in their radii (transverse to the docking axis). Here a one nanometer differential has been simulated, and any conformational change on docking (which might also contribute a detectable and identifiable micro-acoustic wave) is ignored.

In one embodiment, micro-acoustic waves emitted from protein-protein interactions are identified in the time domain, as the emitted acoustic energy may generally be concentrated in short pulses generated by binding events rather than in longer, more tone-like intervals. FIG. 3 shows the results of a calculation based on the principles outlined above: the noise spectrum has been inverted to give a time series, and a short Gaussian pulse (approximately one nanosecond) was used for the source speed $\vec{v}_c$ in Equation 2. The docking was simulated to occur within a few microns of simulated target area surface 150, where the region of detector 135 sensitivity lies. Because the noise spectrum rises with frequency, and the docking pulse spectrum is basically flat, heavy low-pass filtering can be used to boost the SNR, as has been done here in FIG. 3.

Figure 4B:
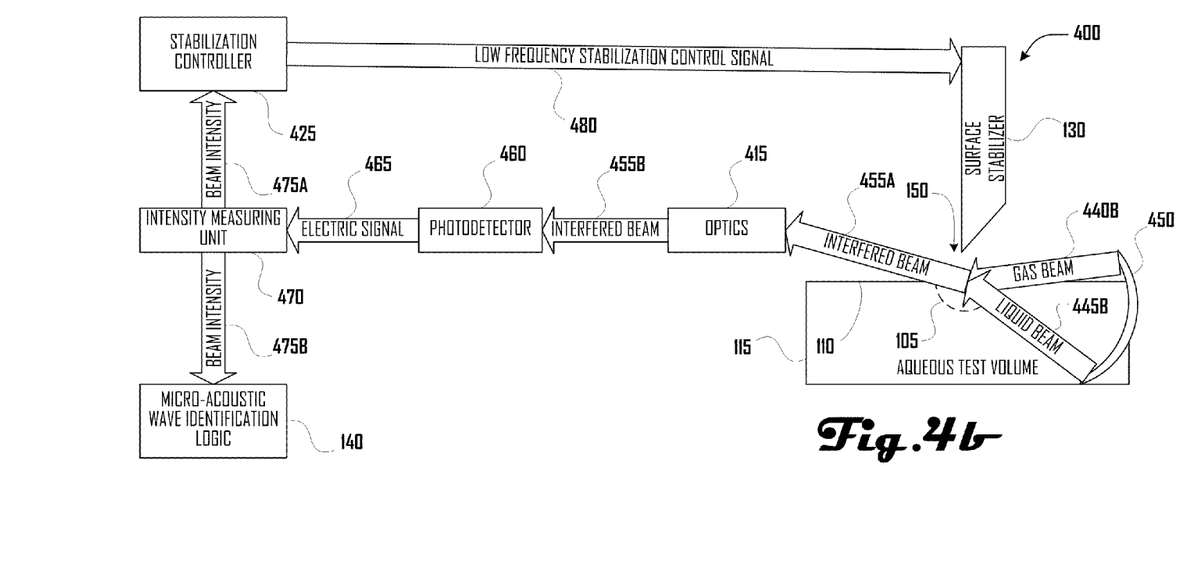

FIGS. 4a and 4b illustrate a laser-interferometer-based micro-acoustic radiation detector 400 in accordance with one embodiment. According to detector 400, elevation changes of the liquid-gas interface at the target area 150 of the free surface 110 of aqueous test volume 115 are converted into relative phase shifts between two interfering beams (e.g., beams 440 and 445). These phase shifts appear as intensity variations in the combined beam (e.g., interfered beam 455), and these variations can be measured and recorded. Thus, device 400 is essentially a Michelson interferometer, adapted to detect micro-acoustic radiation emitted by macromolecular samples (not shown in FIG. 4).

Detector 400 includes a source 405 of steady coherent light, which emits a coherent light beam 410. In some embodiments, the coherence length may be substantially greater than the size of the sample vessel containing aqueous test volume 115. In many embodiments, most gas or diode lasers are suitable as source 405, although multi-mode "ultra-low noise" units may not be. In many embodiments, the laser wavelength may be sufficiently long so as not to break hydrogen bonds in the macromolecule(s) under study, nor to otherwise damage cells. The 635 nm, 5 mW LabLaser (#31-0128-000 from Coherent Inc, Auburn, Calif.) is suitable. The laser may be placed in an aimable mechanical mount to facilitate alignment (e.g., Coherent 0221-449-000). In some embodiments, the laser may have its major polarization axis oriented vertically. In most embodiments, the laser is employed strictly as a measuring instrument and does not transfer appreciable energy and/or heat into the aqueous test volume 115 or the macromolecules under study, nor does the laser typically provoke any motion or other reaction from the macromolecule(s) under study.

Coherent light beam 410 passes through optics 415, which in various embodiments, may expand, isolate, split, focus, and/or steer coherent light beam 410. In one embodiment, optics 415 may include some or all of the exemplary optical components illustrated in FIG. 8, discussed below.

In the illustrated embodiment, optics 415 splits coherent light beam 410 into two components: primary beam 430 and reference beam 420. In one embodiment, primary beam 430 and reference beam 420 may be of at least roughly equal intensity. Reference beam 420 (and/or intensity measurements derived from reference beam 420) is directed to stabilization controller 425 (discussed further below) to eliminate both residual intensity noise produced in the laser cavity (e.g., through mode-hopping), and additional intensity modulation produced by interfering stray reflections in the interferometer.

Primary beam 430 is further steered and/or focused on target area 150 on the liquid/gas boundary surface 110 of aqueous test volume 115. The abrupt increase in refractive index at the target area 150 on the liquid/gas boundary surface 110 causes primary beam 430 to split into two components: gas beam 440A, which reflects off of the target area 150 on the liquid/gas boundary surface 110, and liquid beam 445A, which refracts into the test region 105 of aqueous test volume 115. In one embodiment, primary beam 430 is steered to the target area 150 at an incidence angle of approximately 83.5 degrees (or, equivalently, at a grazing angle of approximately 6.5 degrees), which will cause gas beam 440A and liquid beam 445A to have approximately equal intensities. In other embodiments, primary beam 430 may approach target area 150 at other incidence/grazing angles, which will cause gas beam 440A and liquid beam 445A to have different intensities.

As illustrated in FIG. 4b, both the gas beam 440B and liquid beam 445B are reflected back to the focus point (target area 150 on the liquid/gas boundary surface 110) by at least one mirror 450. In one embodiment, a single spherical mirror 450 may be placed so that its center-of-curvature (as opposed to its focus) coincides spatially with the primary beam 430 focus on target area 150, such that both the gas beam 440A and the liquid beam 445A fall upon it. Although the mirror 450 may be aimed to align the beams properly, it is held fixed during the recording of signals. In other embodiments, two or more fixed mirrors (not shown) may be employed, and/or additional fixed-position optical steering components may be used. Thus, the interferometer design described here differs substantially from other designs, in which the end reflector in one or both arms is allowed to move to produce a signal.

The gas beam 440B and liquid beam 445B, having been split by the abrupt increase in refractive index at the target area 150 on the liquid/gas boundary surface 110, recombine into interfered beam 455A when they reflected back to target area 150. The distance that gas beam 440A-B and liquid beam 445A-B will have traveled will vary slightly according to microscopic elevation changes of the liquid/gas boundary surface 110 at target area 150.

Thus, in this design, the movable element, which causes the relative phase shifts between the two beams, is in fact also the thing that produced the two beams in the first place—i.e., the liquid/gas boundary at the free surface 110 of the aqueous test volume 115. This results in an enhanced sensitivity, relative to the more typical procedure of allowing one of the return reflectors (the mirror 450 in this case) to be movable, as in typical laser interferometers.

For example, when the elevation of the liquid/gas boundary surface 110 at target area 150 rises by a microscopic amount, the gas beam 440A-B is shortened while the liquid beam 445A-B is lengthened, altering the phase shift between the gas beam 440A-B and the liquid beam 445A-B. Conversely, when the elevation of the liquid/gas boundary surface 110 at target area 150 falls by a microscopic amount, the gas beam 440A-B is lengthened while the liquid beam 445A-B is shortened, altering the phase shift between the gas beam 440A-B and the liquid beam 445A-B. The changing phase shifts between the gas beam 440A-B and the liquid beam 445A-B cause the intensity of interfered beam 455 to detectably vary in a manner that corresponds to the microscopic elevation changes of the liquid/gas boundary surface 110 at target area 150. As discussed below in reference to FIGS. 5-7, such microscopic elevation changes of the liquid/gas boundary surface 110 at target area 150 may be caused by micro-acoustic waves emitted by various macromolecular events occurring within rest region 105. Thus, the intensity of interfered beam 455 indicates micro-acoustic radiation propagating through test region 105 (including micro-acoustic waves emitted by various macromolecular events occurring within rest region 105).

Figure 9:
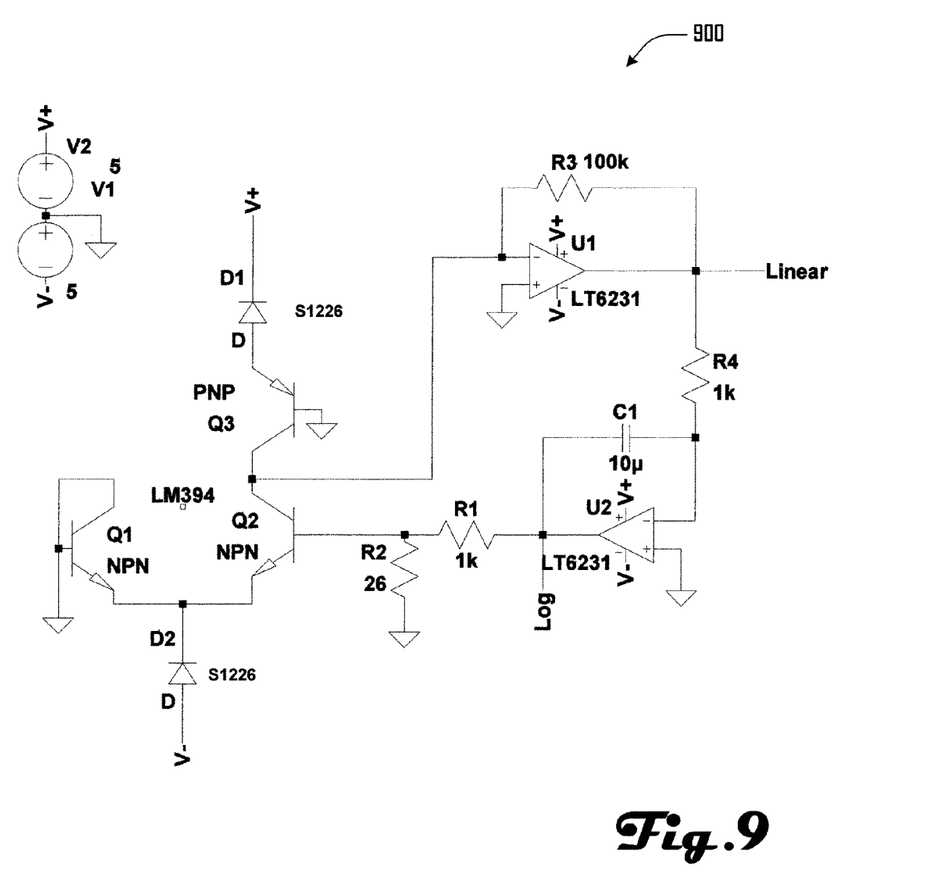
FIG. 9 illustrates an exemplary noise-cancelling circuit such as may be included in a stabilization controller in accordance with one embodiment.

Interfered beam 455A travels back through optics 415, which may re-collimate, steer, and/or otherwise optically process interfered beam 455A. The resulting interfered beam 455B is directed to a photodetector 460, which converts interfered beam 455B to an electric signal 465, which is measured by intensity measuring unit 470. The measured beam intensity 475A (which may be an analog and/or digital signal) is passed to stabilization controller 425, which sends a stabilization control signal 480 to surface stabilizer 130 to stabilize low frequency elevation changes of the target area 150 surface. One embodiment of an exemplary stabilization controller 425 and stabilizer 130 are illustrated in FIG. 9, discussed below.

The measured beam intensity 475B (which may be an analog and/or digital signal) is also passed to logic 140, which identifies a signal corresponding to a micro-acoustic wave emitted by a macromolecular event occurring within test region 105. In various embodiments, logic 140 may include logic for analyzing the measured beam intensity 475B in the time and/or frequency domains. In some embodiments, logic 140 may also include a "library" of micro-acoustic signatures corresponding to various known macromolecular events and logic for comparing signals identified in the measured beam intensity 475B with signatures found in the library.

In many embodiments, acoustic radiation due to macromolecular (or larger) sources in aqueous test volume 115 is expected to occur at frequencies below 10 MHz, with the upper limit determined by the viscosity of aqueous test volume 115 (as discussed above) and typical source sizes and energies. Thus, according to basic digital sampling theory, it may be advantageous in some embodiments for intensity measuring unit 470 and/or identification logic 140 to include a high speed digitization system with a sample rate of at least twice the highest frequency of interest (e.g., 20 MHz or more) for sampling electric signal 465. In some embodiments, the NI-5102 from National Instruments, of Dallas, Tex., may be a suitable high speed digitization system.

Figure 5:
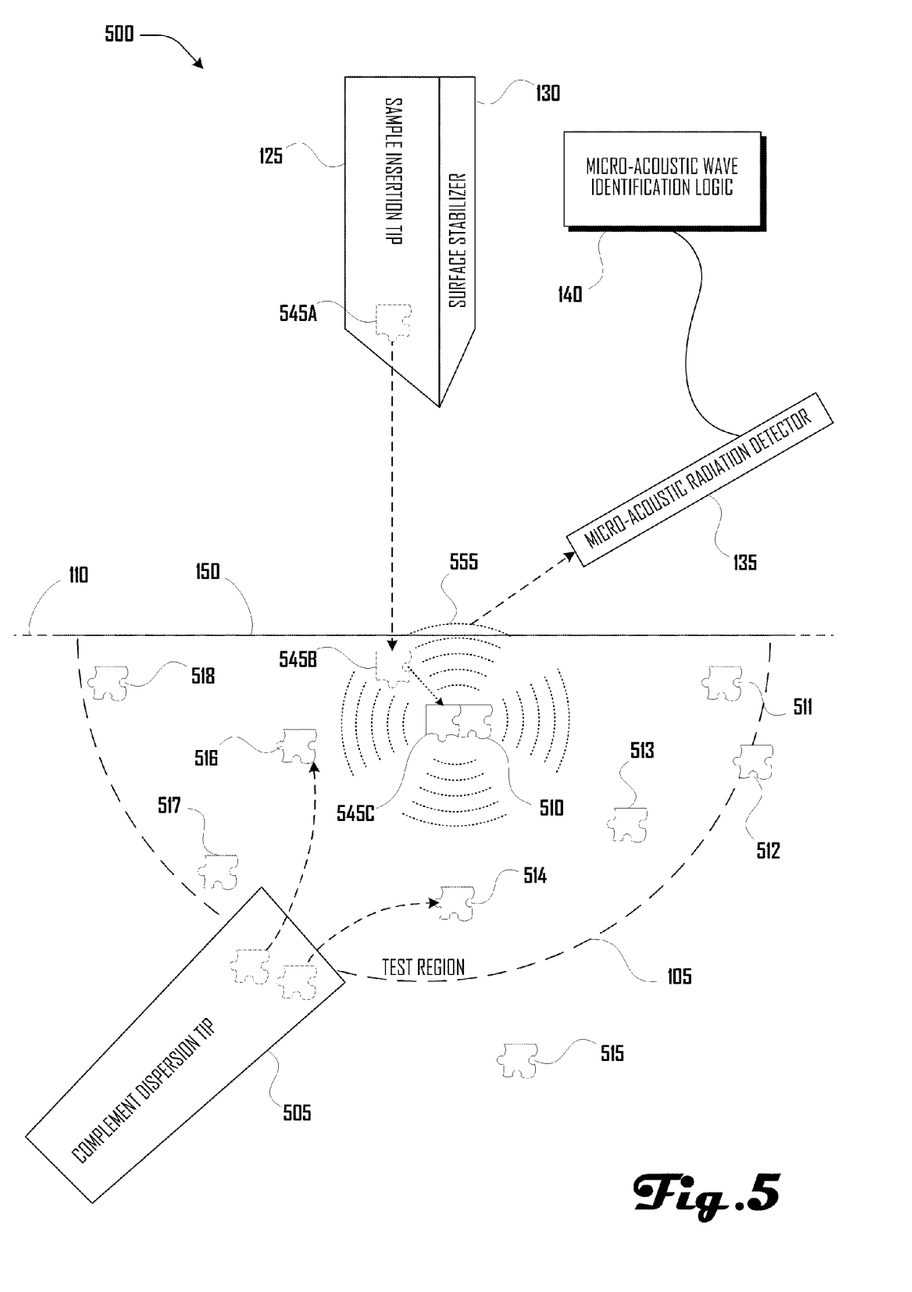
FIG. 5 illustrates an exemplary system for detecting a macromolecular docking event between one or more sample macromolecules and one or more complementary macromolecules in accordance with one embodiment.

FIG. 5 illustrates system 100 adapted as an exemplary system 500 for detecting a macromolecular docking event between one or more sample macromolecule(s) 545 and one or more complementary macromolecules 510-18 in accordance with one embodiment. In system 500, at least one insertable macromolecule 545A leaves sample insertion tip 125 and is introduced (545B) into test region 105. Complement dispersion tip 505 disperses a plurality of complementary macromolecules 510-18 in and around test region 105. The insertable macromolecule 545C docks with a complementary macromolecule 510, emitting a micro-acoustic wave 555, which is detected by detector 135 and identified by logic 140.

For example, in various embodiments, the macromolecular docking event may be between an enzyme macromolecule and an inhibitor macromolecule, between an antibody macromolecule and an antigen macromolecule, between a first type of protein macromolecule and a second type of protein macromolecule, between a protein macromolecule and a nucleic acid macromolecule, and/or between any other macromolecule of a first type and a complementary macromolecule of a second type. In various embodiments, either one of a pair of complementary macromolecule types may be insertable, while the other type may be dispersed. For example, in some embodiments, a plurality of antibody macromolecules may be dispersed in and around test region 105, while one or more antigen macromolecules may be inserted via sample insertion tip 125. Conversely, in other embodiments, a plurality of antigen macromolecules may be dispersed in and around test region 105, while one or more antibody macromolecules may be inserted via sample insertion tip 125.

Figure 6:
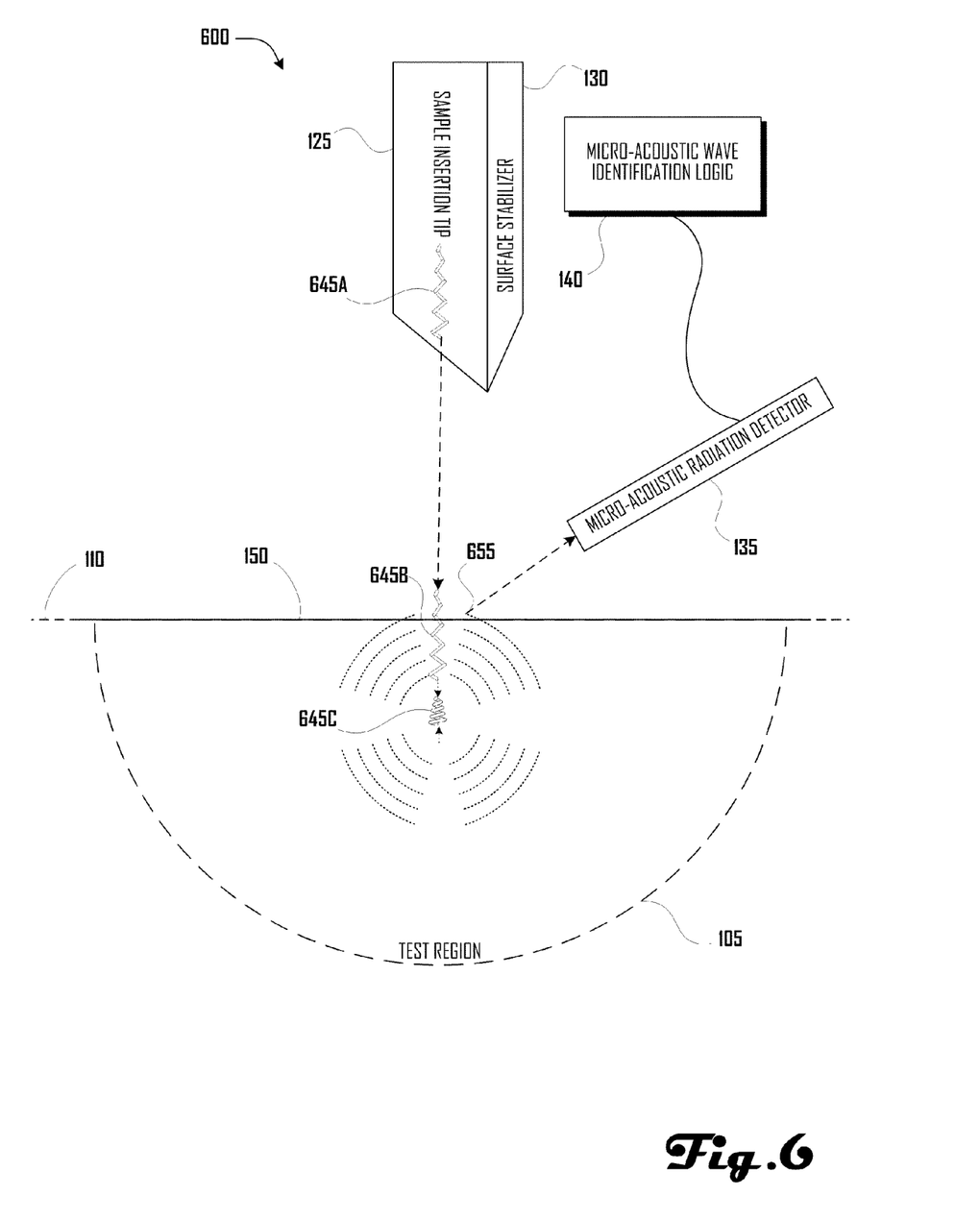
FIG. 6 illustrates an exemplary system for detecting a macromolecular shape-change event in accordance with one embodiment.

FIG. 6 illustrates system 100 adapted as an exemplary system 600 for detecting a macromolecular shape-change event in accordance with one embodiment. In system 600, at least one insertable macromolecule 645A in a first shape and/or conformation leaves sample insertion tip 125 and is introduced (645B) into test region 105, where it is provoked to change (645C) to a second shape and/or shift to a second conformation. The shape and/or conformation changing event releases a micro-acoustic wave 655, which is detected by detector 135 and identified by logic 140.

For example, in one embodiment, an insertable strand of DNA may be introduced into test region 104 and provoked to supercoil. (See also FIG. 2, discussed above.)

For another example, in some embodiments, sample insertion tip 125 may hold one or more denatured protein molecules 645A. In one embodiment, protein molecule 645A may be denatured via heat. In another embodiment, protein molecule 645A may be denatured via a chemical denaturant. In other embodiments, other denaturing agents may be employed. When introduced into test region 105, the denaturant and/or heat diffuses away from the denatured protein molecule 645B, provoking one or more protein folding motions and/or conformational changes to occur, emitting detectable a detectable wave 655 of micro-acoustic radiation.

In some embodiments, a particular type of protein macromolecule may emit micro-acoustic waves 655 that has a characteristic "signature" that may be identified in the time- and/or frequency-domain, which micro-acoustic signature may be used to identify the particular type of protein. For example, one type of protein macromolecule may emit a sequence of "clicks" that are characteristically spaced in time and/or that have characteristically varying amplitudes and/or spectra. Some or all of such characteristic variations may form a micro-acoustic signature that is associated (possibly uniquely) with that type of protein macromolecule.

In embodiments using chemical denaturing compounds, an additional microfluidic input of de-ionized water (not shown) and also a steady drain (not shown) may also be provided to prevent the accumulation of denaturing compounds or other contaminants. In embodiments using heat as a denaturing agent, one or more temperature controllers (not shown) may also be provided to control the temperatures of the sample insertion tip 125 and/or the aqueous test volume in and around test region 105.

Figure 7:
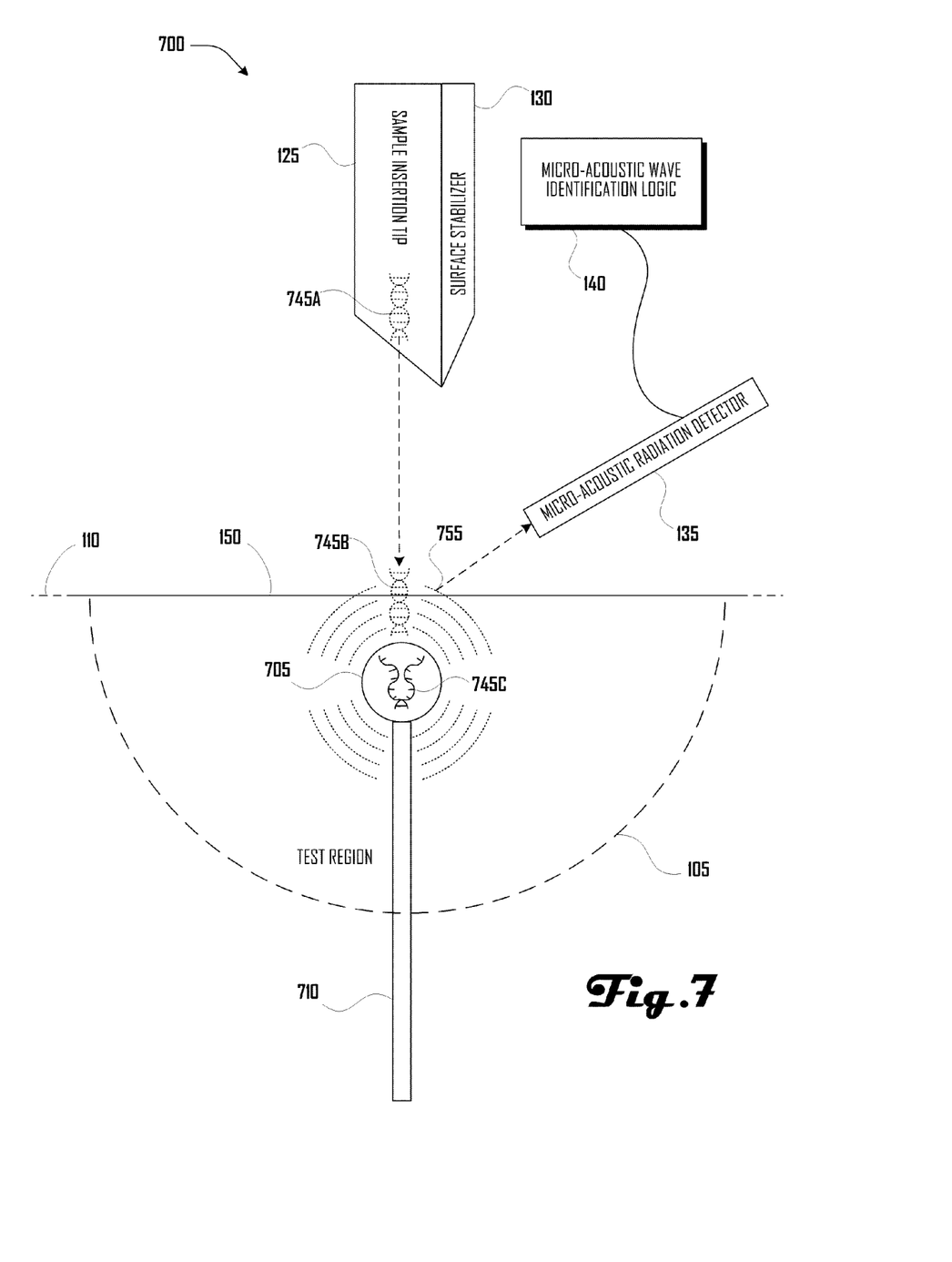
FIG. 7 illustrates an exemplary system for detecting a DNA replication event in accordance with one embodiment.

FIG. 7 illustrates system 100 adapted as an exemplary system 700 for detecting a DNA replication event in accordance with one embodiment. In system 700, one or more insertable strands of DNA macromolecules 745A (e.g., from a target species or individual) leave sample insertion tip 125 and are introduced (745B) into test region 105. Test region 105 includes a replication enzyme complex 705 fixed to a mount 710. For example, in one embodiment, a biotinylated polymerase complex 705 may be bonded to a streptavidin bead affixed to mount 710. Insertable strand of DNA macromolecule 745C interacts with replication enzyme complex 705 in a replication event, which involves substantial motions of the replication enzyme complex 705 and emits micro-acoustic wave 755. Detector 135 detects micro-acoustic radiation propagating through test region 105, and logic 140 identifies the micro-acoustic wave 755 emitted during the replication event.

Once replication begins, one embodiment may be able to discriminate distinct sounds corresponding to the unzipping or shifting of the strand and/or the addition of each base, resulting in long, high quality reads from single, unamplified, untagged molecules. For example, in some embodiments, logic 140 may be able to distinguish between a first portion of micro-acoustic wave 755 corresponding to, e.g., helicase unzipping an A-T base pair and a second portion of micro-acoustic wave 755 corresponding to, e.g., helicase unzipping an C-G base pair.

Figure 8:
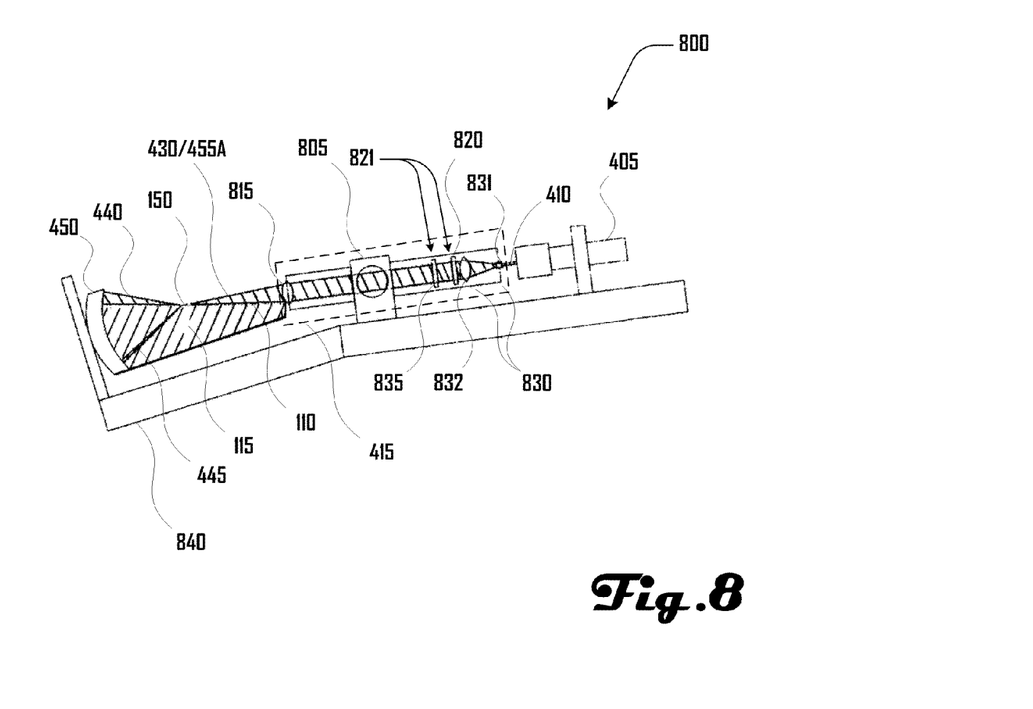
FIG. 8 illustrates various optical components according to one embodiment of a laser-interferometer-based micro-acoustic radiation detector.

FIG. 8 illustrates various optical components (e.g., components of optics 415, as illustrated in FIG. 4, discussed above) of one embodiment 800 of a laser-interferometer-based micro-acoustic radiation detector (e.g., detector 400).

As illustrated in FIG. 8, a coherent beam 410 from a coherent light source 405 may be expanded in diameter via beam expander 830 to improve its focusing properties and increase its immunity to local surface defects in optical elements. A pair of lenses 831-32 may be held in alignment with standard C-mount components, such as those available from Edmund Industrial Optics ("EO") of Barrington, N.J. A small (but somewhat larger than the coherent beam 410) concave lens 831 (e.g., EO 45-373) may be used to make the coherent beam 410 divergent. A larger convex lens 832 (e.g., EO 47-347) collimates the divergent beam. The expansion ratio is equal to the ratio of the focal length of the large lens 832 to that of the small lens 831. In some embodiments, the large lens 832 may be larger than the small lens 831 by somewhat more than this ratio. In some embodiments, some or all lenses may be coated to minimize stray reflections. In other embodiments, a plano-concave lens (not shown) is used and may be oriented so that the concave side faces the coherent light source 405, to spread any residual back-reflection over a large area. The expanded source beam may be put through a polarizer 820 (e.g., EO 47-216) with the transmission axis oriented vertically.

In one embodiment, the expanded and polarized source beam may be passed through a zero order quarter-wave plate 835 tuned for 635 nm (e.g., EO 43-700). The slow axis of the quarter-wave plate 835 may be aligned at 45 degrees from vertical. The quarter-wave plate 835 causes the interfered beam to have a horizontal polarization on return, and thus it will be blocked by the vertical polarizer 820 and prevented from re-entering the laser cavity.

After passing through the optical isolation system 821 (quarter-wave plate 835 and polarizer 820), the source beam may be split into two components: primary beam 430 and reference beam 420 (not shown in FIG. 8; see FIG. 4). In one embodiment, the two components may be of equal intensity. In one embodiment, a thin plate-glass beam splitter 805 (e.g., EO 54-824) with a 50-50 splitting ratio may be used.

Primary beam 430 is further steered and/or focused to target area 150 on the surface 110 of aqueous test volume 115. In one embodiment, a single lens 815 (EO 47-364) in a simple fine focusing mount (EO 03-625) is adequate for this purpose. The focusing lens 815 may be large enough to avoid vignetting the signal beam, and its focal length may be at least approximately 10 times as great as its diameter, so that the lens will be above the water's surface in spite of the low incidence angle of the beam to the water (approximately 83.5 degrees in one embodiment).

In one embodiment, focusing lens 815 also re-collimates the interfered beam 455A. Furthermore, upon reaching the plate beam splitter 805, half of the interfered beam 455B (not shown in FIG. 8; see FIG. 4, discussed above) is steered out of the system in a direction opposite that of the reference beam 420 (not shown in FIG. 8; see FIG. 4, discussed above) towards one or more photodetectors 460 (not shown in FIG. 8; see FIG. 4, discussed above), e.g., a pair of silicon PIN photodiodes such as any of the S1226 series, provided by Hamamatsu Photonics K.K. of Japan. These form the sensing element in a noise-cancelling circuit shown schematically in FIG. 9, discussed below. Mechanically, the photodiodes may be placed as close as possible to the noise cancelling circuitry (described below) without long leads. The remainder (not shown) of the interfered beam 455B passes back thru the quarter-wave plate 835, becomes horizontally polarized, and is then blocked by the vertical polarizer 820.

In one embodiment, some or all the optical components 415 may be mounted to an optical rail 840, e.g., the outside surface of a U-channel, the long dimension of which defines the optical axis. Some or all of the beam expander 830, polarizer 820, isolator 821, plate-beamsplitter 805, and focusing lens 815 may all be assembled into one unit via standard C-mount hardware (2 each of EO 54-611, 56-353, 54-639, 54-615). The aimable mounts for the coherent light source 405 and the mirror 450 may be shimmed to the proper height to align their central axes with the corresponding segments of the optical axis.

In some embodiments, the vessel enclosing aqueous test volume 115 may include optical-quality transmitting surfaces. In one embodiment, mirror 450 may be partially enclosed by collar (not shown), held in place by a clamp (not shown), which in turn compresses an O-ring (not shown) around the edge of mirror 450. In one embodiment, the collar may be of sufficient length to allow it to be filled with aqueous liquid up to the height of the target area 150. The collar is not a closed cylinder, but is open along its top edge, with a gap of 0.5-1 in. With this option, the optical surface of the mirror 450 forms the lower end of the vessel enclosing aqueous test volume 115, and is wet when the vessel is filled. In such an embodiment, the vessel includes no transmitting surfaces.

In other embodiments, the vessel may comprise a small hemispherical glass "bird-bath." Two concentric hemispherical optical surfaces (not shown) are figured in this vessel. In such embodiments, the vessel is placed on a post (not shown) and attached to the optical rail 840, such that the hemispheres' center is coincident with the target area 150. In some embodiments, such a vessel may be made from silanized glass, to flatten the meniscus that would otherwise occur when the vessel is filled. In such embodiments, the spherical mirror 450 remains dry, and the liquid beam 445 is transmitted through two optical surfaces (not shown) before reaching the mirror 450. However, since all rays incident upon these two optical surfaces will be at normal incidence by design, refractive effects will be minimized.

FIG. 9 illustrates an exemplary noise-cancelling circuit 900 such as may be included in a stabilization controller (e.g., controller 425) in accordance with one embodiment. In one embodiment, a pair of photodiodes are arranged electrically in series, with the signal current tapped off from the node between them (or rather between the cascoded PNP transistor Q3 and the signal path half of the adjustable current splitter, Q2). Thus, the signal (labeled "Linear" in FIG. 9) is proportional to the difference between the photocurrents due to the interfered beam 455B (see FIG. 4) and reference beam 420 (see FIG. 4), after amplification by the TIA formed from U1 and R3. In one embodiment, U1 and U2 may be low-noise op-amps, possibly in a monolithic pair, such as the LT6231 from Linear Technology Inc., Milpitas, Calif.

In various embodiments, the reference beam 420 may be brighter than the interfered beam 455B by approximately a factor of four. Therefore, in such embodiments, the signal photodiode D1 may not be able to provide the entire photocurrent required by the reference photodiode D2. However, the reference photodiode draws the additional current it requires through half of a BJT matched pair (e.g., National Semiconductor LM394). The other half of the matched pair is in the current path between the photodiodes, and the two BJT's (Q1 and Q2) are connected such that the current through one is directly proportional to the current through the other, as shown in FIG. 9. The constant of proportionality is determined by the voltage difference between the two BJT bases, which in turn is determined through negative feedback from the signal output itself via U2.

To provide this feedback, the "Linear" signal is fed through R4 to servo amplifier U2, which is locally open-looped at DC (capacitive feedback only, through C1). The "Linear" signal output is thus kept at an average value of zero by adjusting the voltage fed to the base of Q2 (through voltage divider R1 and R2, which prevents a possible lockup condition), out to a frequency determined by the bandwidth of the feedback circuit (less than a few kHz). Since the signal and reference beams are in fact from the same coherent source, their residual intensity noise ("RIN") contributions are also proportional to each other. Thus, by balancing the signal and reference photocurrents at low frequencies, the RIN can be cancelled throughout the bandwidth in which the BJT's remain well-matched (0-100 MHz, typically), which more than covers the bandwidth of interest (0-10 MHz).

It is also possible to cancel RIN in digital data and/or via divider circuitry, again using the interfered beam 455B (see FIG. 4) and reference beam 420 (see FIG. 4). Whatever method is used, in many embodiments, the effects of RIN may be reduced by 40 dB or more in order to detect acoustic radiation from microscopic sources, as described herein.

A signal proportional to the amount of negative feedback required to cancel the RIN is available as a second output (labeled "Log" in FIG. 9). This signal essentially tracks low-frequency mechanical perturbations to the water surface. It can be used to cancel out these perturbations, and to hold the signal beam to a constant mid-level intensity, by using it as an error signal with which to drive a surface stabilizer 130 (see FIGS. 1 and 4, discussed above). In one embodiment, surface stabilizer 130 may comprise a high-voltage sharp-tipped electrode held within 0.5 mm of the water surface, directly above the target area 150. In one embodiment, the tip may be held at an average DC level of approximately 150 V, with perturbations proportional to the force required to steady the water's surface. In one embodiment, these perturbations can be provided by a standard high-voltage differential amplifier, such as the Matsusada AMS 0.6B50 (Matsusada Precision Inc., Kusatsu City, Japan). The precise perturbation needed is indicated by the error signal ("Log" in FIG. 2). The DC level lifts the surface slightly (<1 micron), so that if a downward force is required to keep the surface stationary, it can be provided by surface tension. The lifting occurs due to the attractive force exerted on the electric dipole moments of individual water molecules towards a region of stronger electric field, such as that found near a sharp-tipped electrode.

Although specific embodiments have been illustrated and described herein, it will be appreciated by those of ordinary skill in the art that a whole variety of alternate and/or equivalent implementations may be substituted for the specific embodiments shown and described without departing from the scope of the present disclosure. This application is intended to cover any adaptations or variations of the embodiments discussed herein.

The invention claimed is:

1. A method of detecting a macromolecular docking event between a first macromolecule of a first type and a second macromolecule of a complementary type, the method comprising:
    dispersing a plurality of macromolecules of the first type in a microscopic test region within an aqueous test volume, said microscopic test region including a liquid/gas boundary surface;
    introducing at least one macromolecule of the complementary type into said microscopic test region, said at least one macromolecule of the complementary type docking with at least one of said plurality of macromolecules of the first type within said microscopic test region, said macromolecular docking emitting a micro-acoustic wave into said microscopic test region;
    detecting, via a micro-acoustic radiation detector, micro-acoustic radiation propagating through said microscopic test region; and
    via identification logic, identifying, in said detected micro-acoustic radiation, said micro-acoustic wave emitted by said macromolecular docking;
    wherein the first type is a selected one of a group consisting of an antibody type and an antigen type and the complementary type is the unselected one of said group; and
    wherein detecting said micro-acoustic radiation via said micro-acoustic radiation detector comprises:
        focusing a primary laser beam at a grazing angle at said liquid/gas boundary surface, thereby splitting said primary laser beam into a first beam and a second beam;
        combining said first and second beams into an interference beam; and
        detecting microscopic high frequency elevation oscillations of said liquid/gas boundary surface according to corresponding oscillations in said interference beam.

2. The method of claim 1, further comprising stabilizing microscopic low frequency elevation changes of said liquid/gas boundary surface.

3. The method of claim 2, wherein stabilizing said microscopic low frequency elevation changes of said liquid/gas boundary surface comprises:
    detecting said microscopic low frequency elevation changes; and
    according to said detected microscopic low frequency elevation changes, varying an attractive force exerted on said liquid/gas boundary surface.

4. The method of claim 3, wherein varying said attractive force comprises varying a voltage provided to an electrode positioned within 0.5 millimeters above said liquid/gas boundary surface.

5. An apparatus for detecting a macromolecular docking event between a first macromolecule of a first type and a second macromolecule of a complementary type, the apparatus comprising:
    a plurality of macromolecules of the first type dispersed in a microscopic test region within an aqueous test volume;
    an insertable macromolecule of the complementary type, introduced into said microscopic test region, said insertable macromolecule of the complementary type docking with at least one of said plurality of macromolecules of the first type within said microscopic test region, said macromolecular docking emitting a micro-acoustic wave into said microscopic test region;
    detecting means for detecting micro-acoustic radiation propagating through said microscopic test region;
    logic for identifying in said detected micro-acoustic radiation said micro-acoustic wave emitted by said macromolecular docking; and
    stabilizing means for stabilizing microscopic low frequency elevation changes within a stabilization area on a surface of said aqueous test volume, said stabilization area including a surface boundary of said microscopic test region;
    wherein the first type is a selected one of a group consisting of an antibody type and an antigen type and the complementary type is the unselected one of said group.

6. The apparatus of claim 5, further comprising introduction means for introducing said insertable macromolecule of the complementary type into said microscopic test region.

7. The apparatus of claim 5, further comprising dispersion means for dispersing said plurality of macromolecules of the first type throughout said microscopic test region.

8. An apparatus for detecting a macromolecular docking event between a first macromolecule of a first type and a second macromolecule of a complementary type, the apparatus comprising:
    an aqueous test volume comprising a liquid/gas boundary surface and a microscopic test region, said microscopic test region being partially bounded by a liquid/gas-boundary-surface target area on said liquid/gas boundary surface, said liquid/gas-boundary-surface target area having a radius of less than 50 micrometers;
    a plurality of macromolecules of the first type, dispersed in said microscopic test region;
    an insertable macromolecule of the complementary type, introduced into said microscopic test region, said insertable macromolecule of the complementary type docking with at least one of said plurality of macromolecules of the first type within said microscopic test region, said macromolecular docking emitting a micro-acoustic wave into said microscopic test region;
    a laser interferometer comprising a primary laser beam focused at a grazing angle at said liquid/gas-boundary-surface target area, said laser interferometer adapted to detect micro-acoustic radiation propagating through said microscopic test region;
    logic adapted to identify, in said detected micro-acoustic radiation, said micro-acoustic wave emitted by said macromolecular docking;
    wherein the first type is a selected one of a group consisting of an antibody type and an antigen type and the complementary type is the unselected one of said group.

9. The apparatus of claim 8, wherein said liquid/gas-boundary-surface target area splits said primary laser beam into a first beam passing above said aqueous test volume and a second beam passing through said microscopic test region, said second beam varying in length according to micro-acoustic radiation propagating through said microscopic test region and perturbing the elevation of said liquid/gas boundary surface adjacent to said microscopic test region.

10. The apparatus of claim 9, wherein said laser interferometer further comprises:
    optics located past said aqueous test volume and configured to steer said first and second beams to recombine into an interfered beam indicating said micro-acoustic radiation propagating through said microscopic test region;

a photodetector located past said optics on an axis of said interfered beam and suitable to convert said interfered beam into an electric signal; and at least one intensity measuring unit connected to the output of said photodetector and suitable to measure the intensity of said electric signal, from which intensity said indicated micro-acoustic radiation is detected.

11. The apparatus of claim 10, wherein said optics are further configured to steer said first and second beams back to said liquid/gas-boundary-surface target area; and wherein said liquid/gas-boundary-surface target area is further configured to recombine said first and second beams into said interfered beam.

12. The apparatus of claim 8, further comprising a macromolecular-sample introduction tip positioned within 0.5 mm of said liquid/gas-boundary-surface target area and adapted to introduce said insertable macromolecule of the complementary type into said microscopic test region.

13. The apparatus of claim 12, wherein said macromolecular-sample introduction tip comprises an electrospray ionization needle.

14. The apparatus of claim 8, further comprising a macromolecular dispersion tip positioned within 0.5 mm of said liquid/gas-boundary-surface target area and adapted to disperse said plurality of macromolecules of the first type in said microscopic test region.

15. The apparatus of claim 8, further comprising a stabilization system adapted to control low frequency elevation changes of said liquid/gas-boundary-surface target area.

16. The apparatus of claim 15, wherein said stabilization system comprises:

an electrode positioned within 0.5 mm above said liquid/gas-boundary-surface target area; and a voltage controller adapted to control a voltage provided to said electrode according to an elevation feedback signal provided by said laser interferometer.

17. The apparatus of claim 16, wherein said electrode comprises an electrospray ionization needle adapted to introduce said insertable macromolecule of the complementary type into said microscopic test region.

* * * * *